United States Patent
Choi et al.

(10) Patent No.: US 8,378,812 B2
(45) Date of Patent: Feb. 19, 2013

(54) APPARATUS AND METHOD FOR ASSISTING MEDICATION, MEDICATION BOX, AND MEDICATION STORAGE CONTAINER

(75) Inventors: Jae Hun Choi, Daejeon (KR); Myung Eun Lim, Daejeon (KR); Dae Hee Kim, Daejeon (KR); Sun Lee Bang, Daejeon (KR); Soo Jun Park, Seoul (KR); Seon Hee Park, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 919 days.

(21) Appl. No.: 12/484,302

(22) Filed: Jun. 15, 2009

(65) Prior Publication Data

US 2010/0102955 A1 Apr. 29, 2010

(30) Foreign Application Priority Data

Oct. 24, 2008 (KR) ........................ 10-2008-0104625

(51) Int. Cl.
*G08B 1/08* (2006.01)
*G08B 23/00* (2006.01)

(52) U.S. Cl. ......... 340/539.12; 340/539.11; 340/539.14; 340/573.1

(58) Field of Classification Search .................. None
See application file for complete search history.

(56) References Cited

U.S. PATENT DOCUMENTS

| | | | | |
|---|---|---|---|---|
| 4,695,954 A | * | 9/1987 | Rose et al. | 221/15 |
| 6,985,870 B2 | * | 1/2006 | Martucci et al. | 705/3 |
| 7,602,275 B2 | * | 10/2009 | Dishongh et al. | 340/309.16 |
| 7,782,189 B2 | * | 8/2010 | Spoonhower et al. | 340/539.12 |
| 2003/0135388 A1 | * | 7/2003 | Martucci et al. | 705/2 |
| 2003/0160698 A1 | * | 8/2003 | Andreasson et al. | 340/573.1 |
| 2004/0104271 A1 | * | 6/2004 | Martucci et al. | 235/472.01 |
| 2005/0280544 A1 | * | 12/2005 | Mishelevich | 340/573.1 |
| 2007/0008112 A1 | * | 1/2007 | Covannon et al. | 340/539.12 |
| 2008/0059228 A1 | * | 3/2008 | Bossi et al. | 705/2 |
| 2009/0043605 A1 | | 2/2009 | Imai et al. | |
| 2010/0052900 A1 | * | 3/2010 | Covannon et al. | 340/539.12 |
| 2012/0102434 A1 | * | 4/2012 | Zerhusen et al. | 715/835 |

FOREIGN PATENT DOCUMENTS

| | | |
|---|---|---|
| JP | 10-201827 A | 8/1998 |
| JP | 2001-070405 A | 3/2001 |
| JP | 2005-013488 A | 1/2005 |
| JP | 20040073560 A | 10/2006 |
| JP | 20070001285 A | 1/2007 |
| WO | 03/060805 A2 | 7/2003 |
| WO | 2005/109119 A2 | 11/2005 |

\* cited by examiner

*Primary Examiner* — Julie Lieu
(74) *Attorney, Agent, or Firm* — Ladas & Parry LLP

(57) ABSTRACT

An apparatus and method for assisting medication are capable of assisting medication of users who have to regularly take medications in daily life. The apparatus includes a medication box having a plurality of containers, each of which stores a dose of medication to be taken at one time according to a medication schedule, a radio frequency (RF) transmitter carried on a user and transmitting an RF signal, an RF receiver receiving the RF signal from the RF transmitter, and a controller controlling medication assisting. Thus, the apparatus checks a spatial-temporal situation of the user, i.e. an medication, notification or information situation, using the received RF signal, and creating and providing medication service corresponding to the checked situation.

15 Claims, 9 Drawing Sheets

APPARATUS AND METHOD FOR ASSISTING MEDICATION, MEDICATION BOX, AND MEDICATION STORAGE CONTAINER

CROSS-REFERENCE TO RELATED APPLICATIONS

This application claims the priority of Korean Patent Application No. 2008-104625, filed on Oct. 24, 2008, in the Korean Intellectual Property Office, the disclosure of which is incorporated herein by reference.

BACKGROUND OF THE INVENTION

1. Field of the Invention

The present invention relates to medication, and more particularly, to an apparatus and method for assisting medication, a medication box, and a medication storage container in a system for assisting medication, designed to assist medication in individuals who have to regularly take medications in daily lives.

2. Description of the Related Art

Patients with chronic illnesses and the elderly have to continue regularly taking medications on time in their daily lives.

However, the older people may have difficulty in following medication schedule (i.e., continuously taking medication on schedule) due to memory failure. For this reason, many regimens for systematically assisting medication have recently been developed, such that older people can readily adapt themselves to medication schedules and take an accurate dose of medication on time.

The regimens developed for assisting medication have turned out to be considerably effective when actually applied to the elderly.

Among the regimens for assisting medication, a representative regimen includes an apparatus for assisting medication, such as a medication bottle or box to which a clock and an alarm are attached. If a time to take a medication is set, this apparatus for assisting medication informs the medication user to take their medication through sound or voice at the set time. In addition to this apparatus, there are many apparatuses, such as dispensers, for automatically dispensing medications at a set time when the medication user has to take their medication.

Nevertheless, these apparatuses inform the user of the medication regardless of the situation of the user. For example, these apparatuses do not take into consideration the individual circumstances of users such as hearing-impaired people who cannot hear the signal given by each apparatus.

Further, these apparatuses merely recognize that a medication is taken when the user pushes down a specific button of each apparatus or opens a cover of each apparatus, and thus cannot check whether or not the user actually took a fixed dose of medication as well as whether or not the medication was actually discharged from the medication box.

SUMMARY OF THE INVENTION

An aspect of the present invention provides an apparatus and method for assisting medication, a medication box, and a medication storage container that can improve the adaptability to medication of users who have to regularly take medications in daily life by assisting the medication of medication users according to a medication situation of each user.

Another aspect of the present invention provides an apparatus and method for assisting medication, a medication box, and a medication storage container that can check the spatial-temporal situation of a user and notify the user of medication on the basis of the checked situation so the user can take an accurate dose of medication on time.

A further aspect of the present invention provides an apparatus and method for assisting medication that can detect a time when a medication is actually discharged, check whether or not the medication is taken, and notify the checked result.

According to an aspect of the present invention, there is provided an apparatus for assisting medication comprising: a medication box storing medications in units of dose to be taken at one time according to a medication schedule; a radio frequency receiver receiving a radio frequency signal from a radio frequency transmitter carried on a user, and extracting radio frequency signal information including information for recognizing the user from the received radio frequency signal; a controller receiving the radio frequency signal information extracted by the radio frequency receiver, creating and providing medication services based on a spatial-temporal situation of the user which are checked using the received radio frequency signal information, and detecting discharge of the medication from the medication box to check whether or not the user takes the medication; and a display unit displaying a result of checking whether or not the user takes the medication and information about the medication services.

According to another aspect of the present invention, there is provided a medication box comprising: a plurality of medication storage containers, each of which stores a dose of medication to be taken at one time according to a medication schedule and includes an infrared sensor for detecting whether or not the stored medication exists; at least one light emitting diode allocated to each medication storage container, and showing a medication situation of the medication stored in each medication storage container; and a liquid crystal display notifying the medication of the medication stored in each medication storage container according to the medication schedule.

According to another aspect of the present invention, there is provided a medication storage container comprising: a medication storage compartment storing a dose of medication to be taken at one time according to a medication schedule; an infrared transmitter installed on one side of the medication storage and transmitting infrared radiation; and an infrared receiver installed on the other side of the medication storage, receiving the infrared radiation transmitted from the infrared transmitter, and generating an output voltage for determining whether or not the medication stored in the medication storage exists on a basis of an amount of the received infrared radiation.

According to another aspect of the present invention, there is provided a method for assisting medication using an apparatus for assisting medication having a medication box. The method comprises: extracting radio frequency signal information including information for recognizing a user from a radio frequency signal received from the user; recognizing the user using the extracted radio frequency signal information, and checking a spatial-temporal situation of the recognized user; examining a present state of each medication storage container of the medication box in which the medications to be taken by the recognized user are stored; creating medication services based on the recognized situation; and providing the created medication services.

BRIEF DESCRIPTION OF THE DRAWINGS

The above and other features and advantages of the present invention will become more apparent to those of ordinary skill in the art by describing in detail exemplary embodiments thereof with reference to the attached drawings in which.

DETAILED DESCRIPTION OF THE EXEMPLARY EMBODIMENTS

The present invention will now be described more fully with reference to the accompanying drawings, in which exemplary embodiments of the invention are shown. Detailed descriptions of known functions and components will be omitted when it is deemed that such description would detract from the clarity and conciseness of the disclosure of the present invention.

In the exemplary embodiments of the present invention, an apparatus and method for assisting medication in a system for assisting the medication on the basis of a medication situation of an individual will be described. First, the system for assisting medication and the apparatus for assisting medication of the system for assisting medication will be described in greater detail with reference to the attached drawings.

Figure 1:
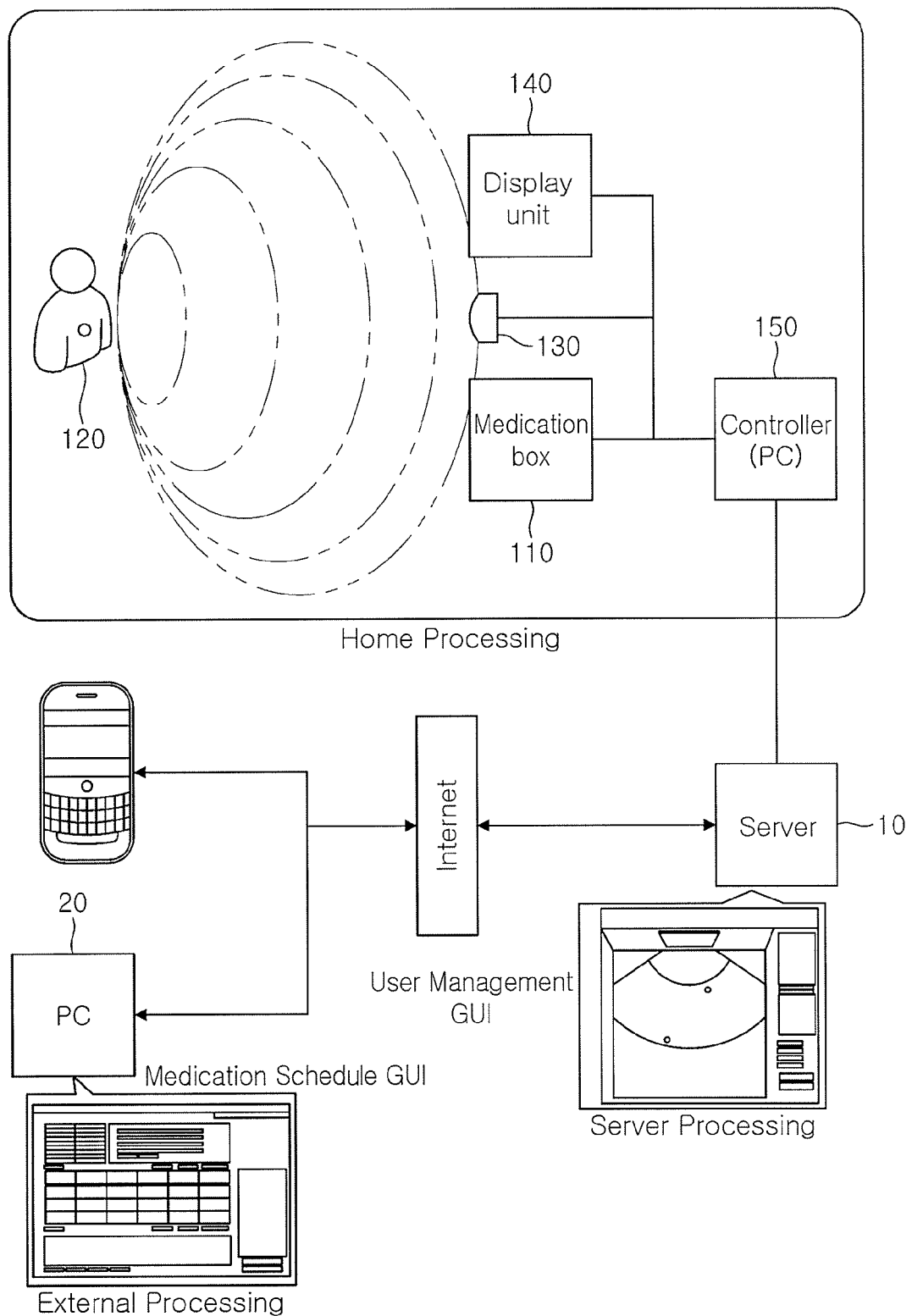
FIG. 1 illustrates the structure of a system for assisting medication according to an exemplary embodiment of the present invention.

FIG. 1 illustrates the structure of a system for assisting medication according to an exemplary embodiment of the present invention.

Referring to FIG. 1, the system for assisting medication includes a server 10 connected to a portable device and transmitting a notification of medication to the portable device, an external personal computer (PC) 20 transmitting a medication schedule inputted at a hospital or pharmacy to the server 10, and an apparatus for assisting medication 100 installed at home.

The apparatus for assisting medication 100 includes a medication box 110, a radio frequency (RF) transmitter 120, an RF receiver 130, a display unit 140, and a controller 150.

Figure 2:
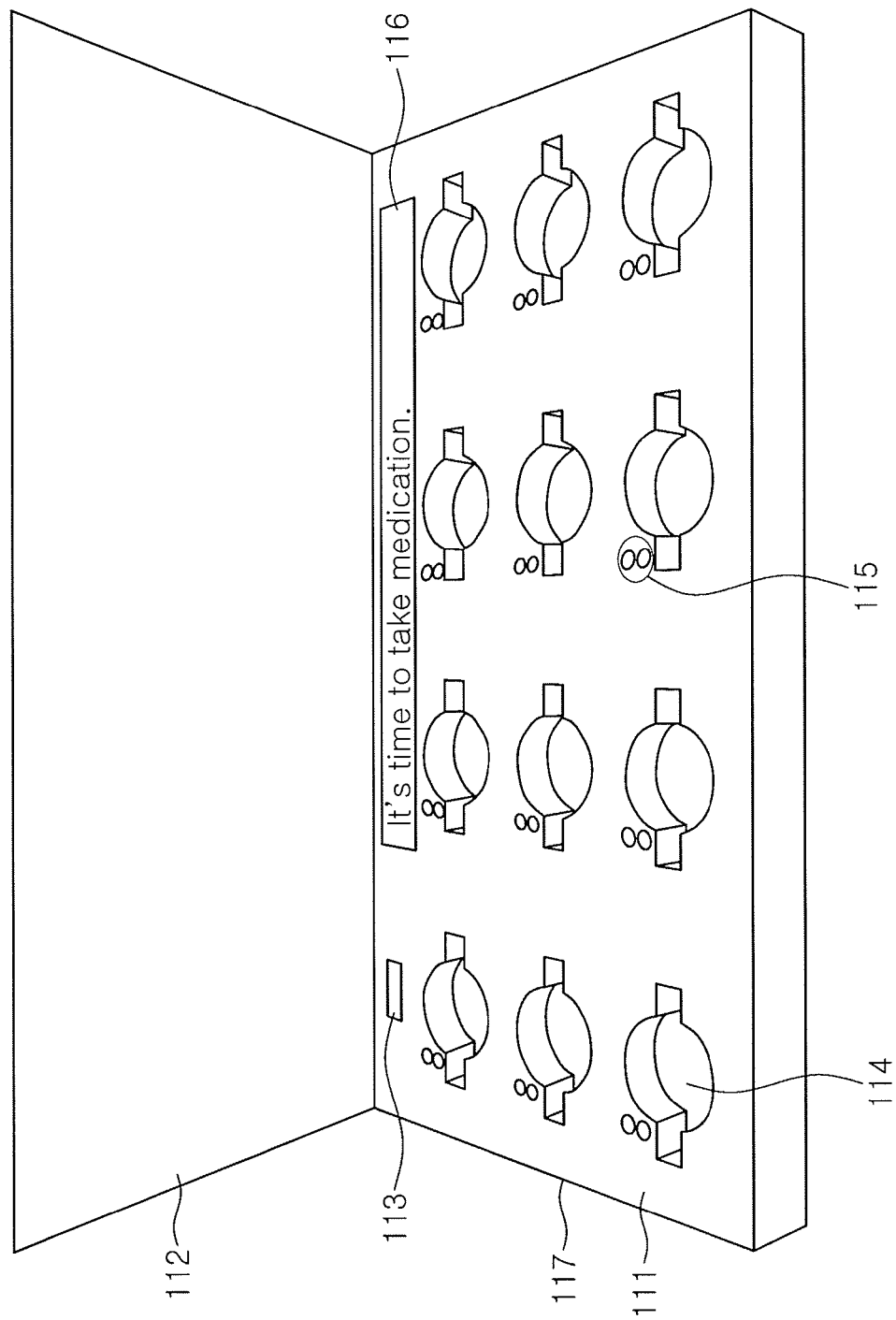
FIG. 2 illustrates the detailed structure of a medication box of an apparatus for assisting medication according to an exemplary embodiment of the present invention.

The medication box 110 includes medication storage containers (hereinafter, referred to as containers) each of which stores a medication prescribed to be taken at one time according to a medication schedule, and a detailed structure thereof is as illustrated in FIG. 2. Referring to FIG. 2, the medication box 110 includes a body 111, a cover 112, a power supply 113, a plurality of containers 114 each of which stores a respective medication, light emitting diodes (LEDs) 115 allocated to the respective containers 114 in pairs, a liquid crystal display 116 capable of outputting a message, and a sender 117 of a universal serial bus (USB) type.

The cover 112 covers the entire body 111, and protects the medications from the outside. The power supply 113 controls the supply of power.

Figure 3:
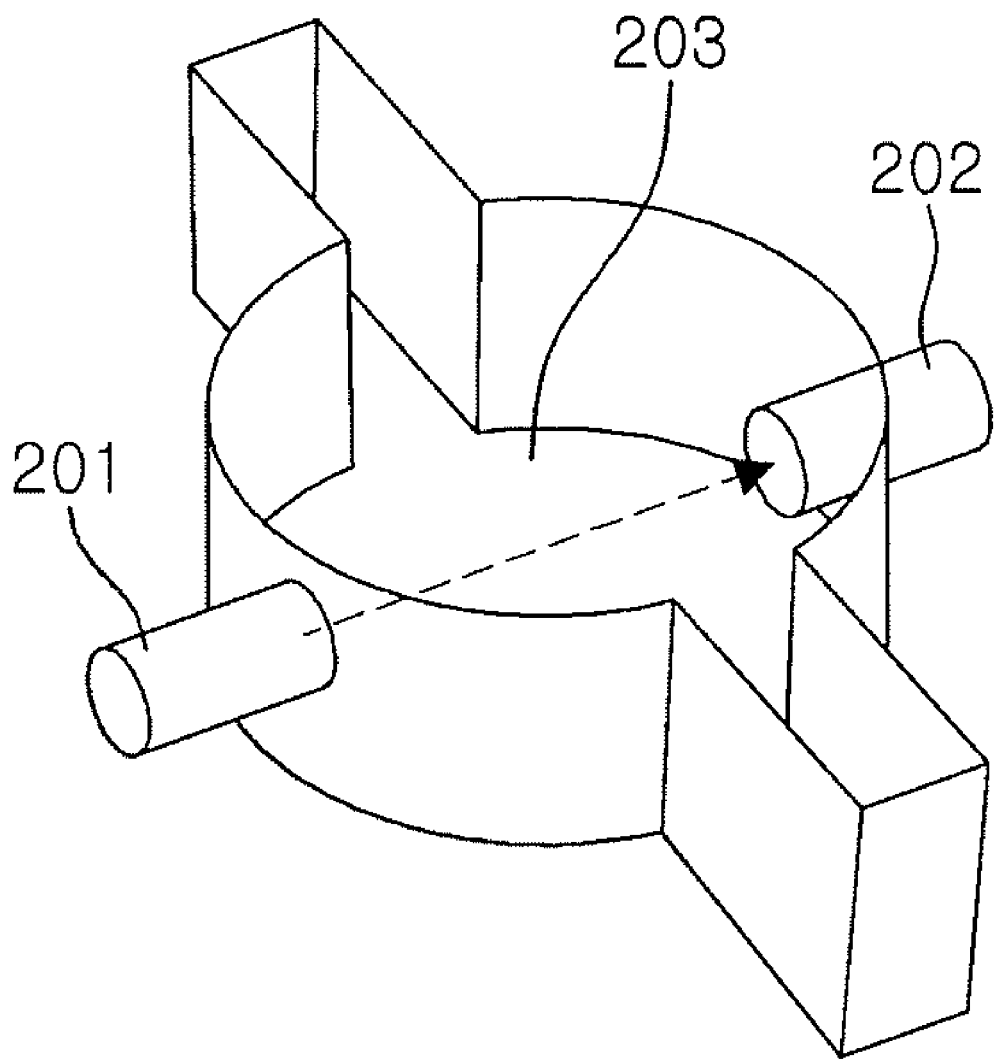
FIG. 3 illustrates a detailed structure of the container illustrated in FIG. 2.
Figure 4A:
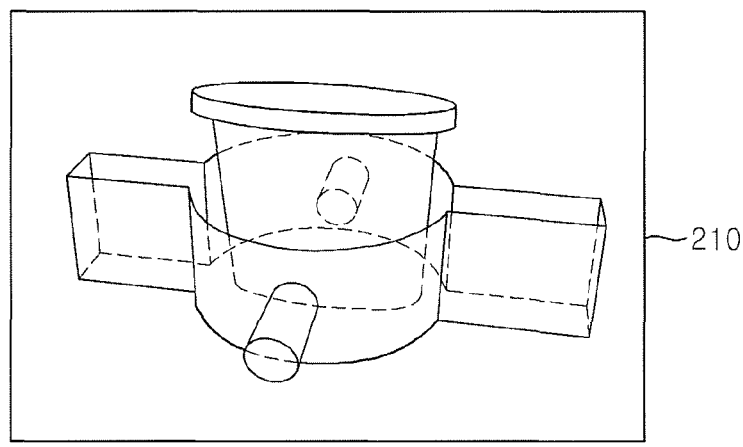
FIGS. 4A through 4C illustrate various shapes of the container illustrated in FIG. 3.
Figure 4B:
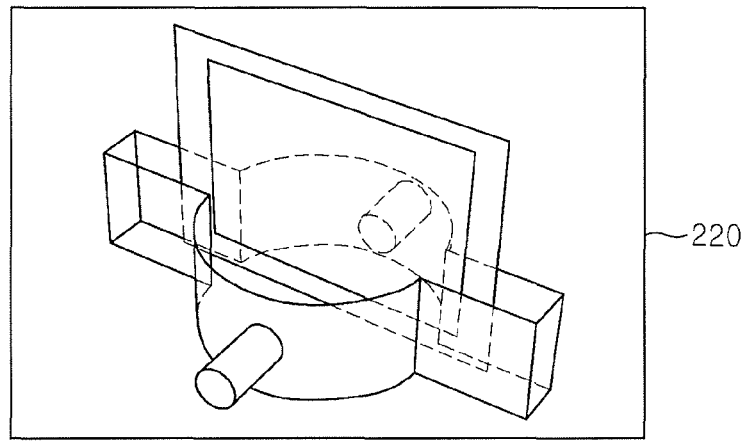
Figure 4C:
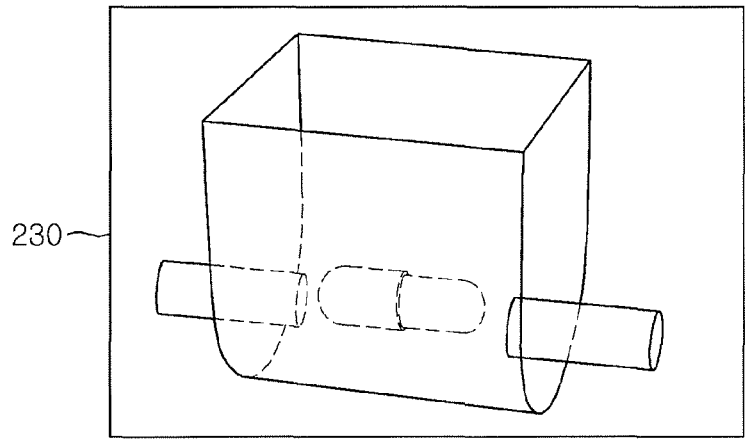
Figure 5:
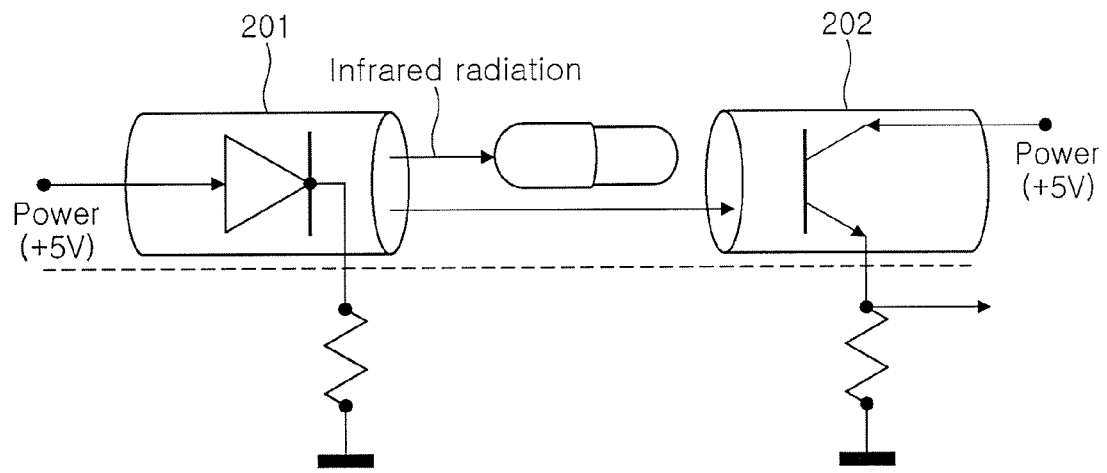
FIG. 5 illustrates the structure of an infrared sensor detecting whether or not a medication is stored in a container in accordance with an exemplary embodiment of the present invention.

As illustrated in FIG. 3, each container 114 includes an infrared transmitter 201, an infrared receiver 202, and a medication storage compartment 203 storing a dose of medication to be taken at one time according to the medication schedule. It is possible to detect whether or not the medication exists on the basis of an amount of infrared radiation transmitted from the infrared transmitter 201 and then striking the infrared receiver 202. Further, each container 114 stores a medication to be taken at one time, and can be modified in various forms depending on a kind of medication to be stored. For example, as illustrated in FIGS. 4A through 4C, each container can be modified into a shape 210 that stores a small medication bottle, a shape 220 that stores a paper medication bag, and a shape 230 that stores several tablets. Here, the infrared transmitter 201 and the infrared receiver 202 of each container 114 are implemented as an infrared sensor, as illustrated in FIG. 5. When receiving infrared radiation emitted by the infrared transmitter 201, the infrared receiver 202 generates an output voltage for determining whether or not the medication exists on the basis of an amount of received infrared radiation. In detail, when a large amount of infrared radiation is received, the output voltage of the infrared receiver 202 of the container 114 has a high level (e.g. +5V). In contrast, when a small amount of infrared radiation is received, the output voltage of the infrared receiver 202 of the container 114 has a low level (e.g. 0V). Thus, when an obstacle such as a medication bottle, a medication paper bag or tablets is disposed between the infrared transmitter 201 and the infrared receiver 202, the voltage has a relatively low level, so that it can be determined whether or not the medication to be taken exists in the container 114.

The LEDs 115 are allocated to the respective containers 114 in pairs, and show a situation related to the medication of the stored medications. In detail, the LEDs 115 can indicate that the medication user has to take certain action, or that the individual does not need to take certain action at present because the medication to be taken in the future is stored. According to these situations, the LEDs 115 can be set to different colors by the controller 150. Although this embodiment has been described taking a pair of LEDs by way of example as illustrated in FIG. 2, only a single LED may be used so as to be turned on when the medication to be taken at present exists or to be turned off when the medication to be taken at present does not exist, namely when the medication has been taken.

The liquid crystal display 116 visualizes various medication notification services using a text.

The sender 117 can employ a USB, and sends/receives information about the state of the medication box 110. In detail, the sender 117 sends the current state of the medication box 110 to the controller 150, or receives data from the controller 150 to allow the state of the medication box 110 to be varied.

Meanwhile, the RF receiver 130 receives an RF signal from the RF transmitter 120 carried on the medication user, processes the received RF signal, extracts identification (ID) of the RF transmitter 120 and the strength of the RF signal from the processed RF signal, and transmits RF signal information, which includes the extracted ID of the RF transmitter 120 and the extracted strength of the RF signal, to the controller 150.

When receiving the RF signal information from the RF receiver 130, the controller 150 checks the spatial-temporal situation of the medication user using the received RF signal information, and creates and provides a medication service according to the checked situation. The controller 150 can use a personal computer (PC), or the like, and receive output voltage from each container 114 to determine whether or not the medication exists through the received output voltage. Here, the determination of whether or not the medication exists is based on the output voltage of each container 114. More specifically, when the output voltage of a specific container 114 is abruptly raised, it is determined that the medication does not exist in the specific container 114, namely that the user has taken the medication. Further, the controller 150 controls the medication box 110 and the display unit 140 to notify the medication user of the medication.

Particularly, the controller 150 recognizes an individual medication user and the distance from the user using the RF signal information. In other words, the controller 150 searches for the ID of the RF transmitter 120 included in the RF signal information on a preset medication user mapping table as in Table 1 below, thereby recognizing the user. Further, the controller 150 searches for the strength of the RF signal included in the RF signal information on a preset distance mapping table as in Table 2 below, thereby recognizing the distance. (Move the line below to the next page)

TABLE 1

| User | ID of RF Transmitter | ID of Medication Box |
|------|----------------------|----------------------|
| A    | 1                    | 10                   |
| B    | 2                    | 20                   |
| ...  | ...                  | ...                  |

TABLE 2

| RF (dBm) | Distance (m) | Situation |
|----------|--------------|-----------|
| 90-75    | 0-1          | Reciprocal Distance |
| 75-55    | 1-5          | Discriminable Distance |
| 55-40    | 5-10         | Recognizable Distance |
| >0       | 10<          | Maximum Distance |

Now, a method for assisting medication in this system for assisting medication using the apparatus for assisting medication will be described in detail with reference to the attached drawings. First, a process of checking a present situation through a surrounding state associated with the medication user at the controller 150 of the apparatus for assisting medication 100 will be described.

Figure 6:
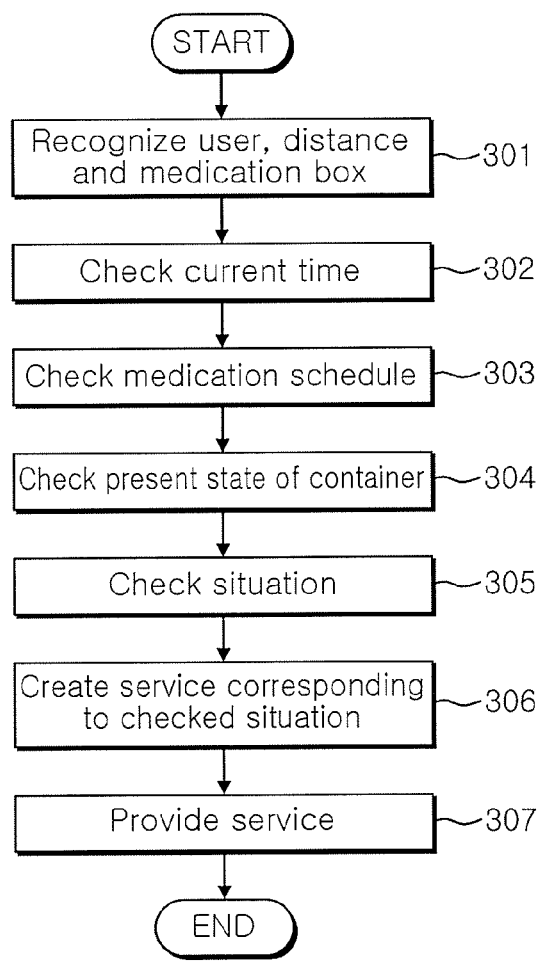
FIG. 6 is a flowchart illustrating a process of checking a present situation in accordance with an exemplary embodiment of the present invention.

FIG. 6 is a flowchart illustrating a process of checking a present situation in accordance with an exemplary embodiment of the present invention.

Referring to FIG. 6, the RF receiver 130 of the apparatus for assisting medication 100 receives an RF signal from the RF transmitter 120 carried on the user, and transmits RF signal information, which is extracted from the received RF signal, to the controller 150. Thus, in step 301, the controller 150 of the apparatus for assisting medication 100 checks the ID of the RF transmitter 120 and strength of the RF signal, both of which are included in the RF signal information received from the RF receiver 120, thereby recognizing the medication user, the medication box and the distance between the medication user and the medication box. In detail, the controller 150 searches for the IDs of the corresponding medication user and the medication box mapped to the ID of the RF transmitter 120 on the user mapping table, and recognizes the searched IDs of the medication user and the medication box as the user who has to take medications and the medication box in which the medications are stored. Further, the controller 150 searches for a distance mapped to the strength on the user mapping table, and recognizes the searched distance as the distance between the user and the medication box.

In step 302, the controller 150 checks a current time. In step 303, the controller 150 checks the medication schedule of the recognized medication user among the medication schedules that are received and pre-stored from the external PC 20 through the server 10. In step 304, the controller 150 checks a present state of the corresponding container 114 allocated to the recognized medication user. Here, the present state of the corresponding container 114 refers to whether or not the medication exists in the container 114, and colors of the LEDs 115. Then, in step 305, the controller 150 checks the situation of the recognized user through data (of the user, the medication box ID, the distance between the user and the medication box, the current time, the medication schedule, the state of the container, etc.) obtained in steps S301 through S304.

In step 306, the controller 150 creates services for medication, notification, information, etc. on the basis of the recognized situation. Then, in step 307, the controller 150 transmits the created services to the user using multimedia.

The data obtained through this process, i.e. the data related to the medication schedule and the present state of the corresponding container 114, is preset on a first situation table. One example of the first situation table is as shown in Table 3 below.

TABLE 3

| Date       | Medicaton time | Container No. | Container State      | Taken? |
|------------|----------------|---------------|----------------------|--------|
| 2008.05.21 | 9:00-9:30      | 1             | FILL = n<br>LED = n  | Y      |
| 2008.05.21 | 12:00-12:30    | 2             | FILL = n<br>LED = n  | N      |
| 2008.05.21 | 18:00-18:30    | 3             | FILL = y<br>LED = n  | N      |

Table 3 shows examples of the user U, the distance D, the current time CT, the medication schedule of a pillbox P, and the present state of the container 114 of the medication box 110. In the present state of the container 114 of Table 3, "FILL=n" indicates that no medication exists, "FILL=y" indicates that a medication exists, and "LED=n" indicates the present color of the LED 115 allocated to the corresponding container 114. Further, the option "Taken?" is a record on whether or not the user took the medication stored in the corresponding container 114 on time. For example, the present state of the container of No. 1 indicates "FILL=n," and thus no medication exists in the container of No. 1 at present, because the user took the medication at a medication time of "9:00-9:30."

Further, conditions and types of services according to a situation are preset in a second situation table. One example of the second situation table is as shown in Table 4 below.

TABLE 4

| Situation | Condition | Type of Service |
|---|---|---|
| Medication | (!Notification situation or !corresponding container) FILL = n | Improperly taken |
| Medication | Notification Situation & corresponding container FILL = n | Properly taken |
| Notification | CT is included in specific schedule time & corresponding container FILL = y | Arrival of medication time |
| Notification | CT is not included in specific schedule time & corresponding container FILL = y | Lapse of medication time |
| Information | Free of the other situations & D > 1 | Long distance |
| Information | Free of the other situations & D < 1 | Short distance |

Table 4 shows the conditions for inferring three types of medication situations, and the types of services depending on the conditions. Here, the medication situations are classified as medication, notification, and information situations. The medication situation is divided into a situation where a qualified user gets access to a medication box to take a desired medication out of the corresponding container 114, and otherwise. The notification situation is divided into a situation where the arrival of medication time is notified, and a situation where the lapse of medication time is notified. For example, if there is a container 114 matched with a specific schedule at a current time, and if a medication is stored in this container 114, there occurs a situation where the arrival of medication time is notified. Further, if medication remains in the corresponding container 114 in spite of the lapse of a predetermined time (t), there occurs a situation where the lapse of medication time is notified. The information situation refers to a situation where, when the user approaches the medication box under an environment that the other situations do not take place, information about medication schedule and medication state of that day is periodically provided.

Now, the processes of generating services on the basis of the three medication situations (medication, notification, and information) during checking a present situation as illustrated in FIG. 6 will be described in detail with respect to each situation. First, the process of recognizing the medication situations to generate a corresponding service will be described in detail with reference to the attached drawings.

Figure 7:
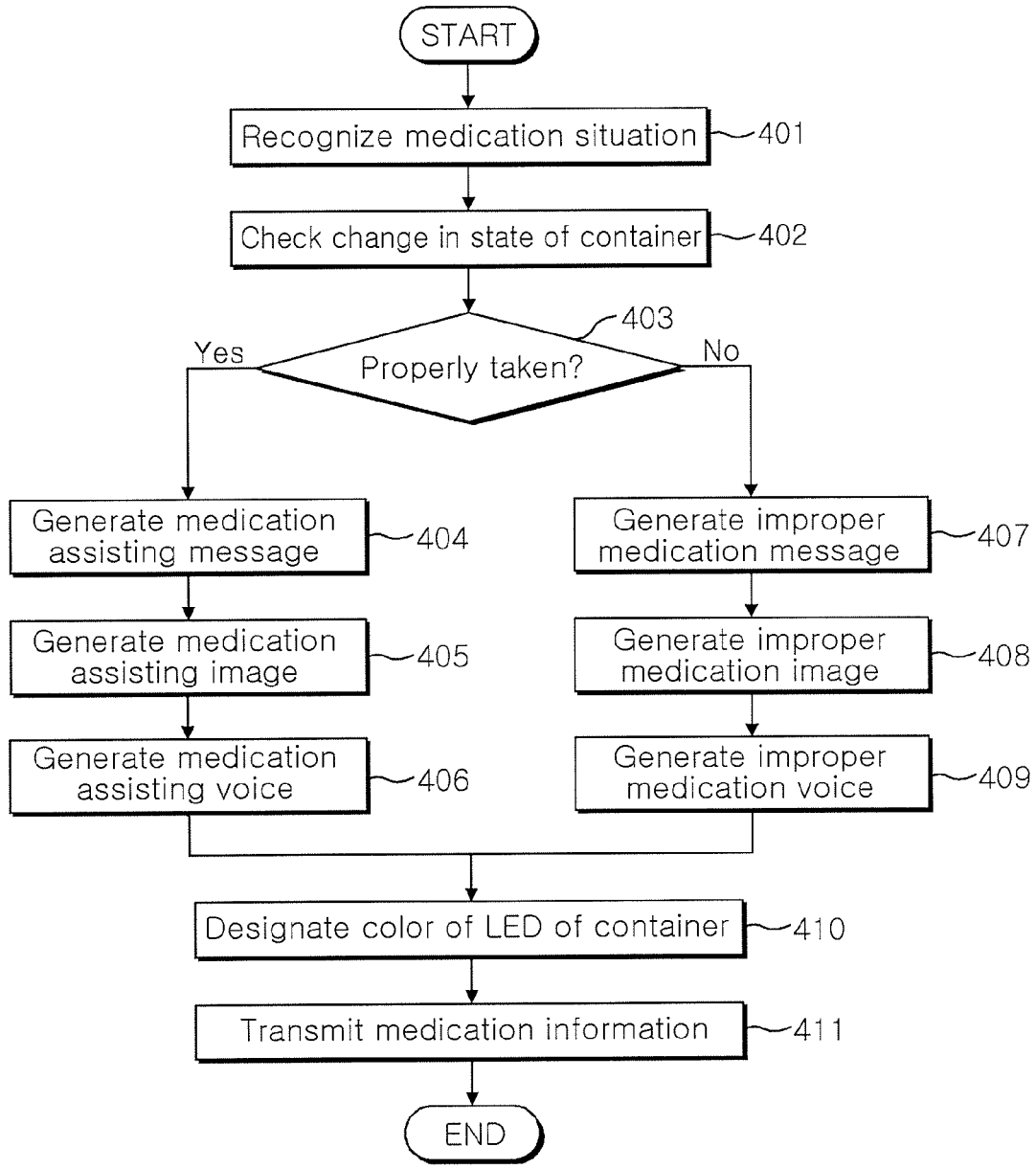
FIG. 7 is a flow chart illustrating a process of generating a service based on recognition of a medication situation in accordance with an exemplary embodiment of the present invention.

FIG. 7 is a flow chart illustrating a process of generating a service based on recognition of a medication situation in accordance with an exemplary embodiment of the present invention.

Referring to FIG. 7, in step 401, the controller 150 of the apparatus for assisting medication 100 recognizes a present situation as a medication situation using state data including the user ID, distance and medication box ID recognized in step 301 of FIG. 6, the medication schedule of the medication box, and the state of the container.

In step 402, the controller 150 compares previous and present states of all the containers 114 of the medication box using the state data, and searches for the containers 114, the state of each of which is changed. Then, in step 403, the controller 150 checks the type of service, and determines whether or not a qualified user takes a proper medication out of a corresponding container 114, namely whether or not the service is the proper medication. Here, the controller 150 checks whether or not the ID of the user who comes nearest the medication box 110 and the container 114 undergoing the change of its state are matched with those of the user mapping table of Table 1. If not so, the controller 150 determines the service to be improper medication. Further, when the medication which the user takes out of the container is not allowed to be taken at present, the controller 150 also determines the service to be improper medication. In contrast, the controller 150 determines the other cases than the aforementioned cases to be proper medication.

As a result of the determination of step 403, when the service is determined to be a proper medication, the controller 150 generates a medication assisting message of a text type regarding a method of medication and precautions in step 404, and a medication assisting image for displaying details associated with the message in an image form instep 405. Then, in step 406, the controller 150 extracts and generates a medication assisting voice capable of guiding the medication through a loudspeaker (not shown) from a voice medication database (not shown), and then proceeds to step 410. Here, the voice medication database is a memory unit that is installed in the server 10, and stores all types of voice available for the medication service.

In contrast, as a result of the determination of step 403, when the service is determined to be an improper medication, the controller 150 generates a warning message, i.e. an improper medication message, of a text type capable of notifying that the medication which the user takes out of the container 114 is not allowed to be taken at present in step 407, and then a warning image, i.e. an improper medication image, capable of notifying the medication user that the medication which the medication user takes out of the container 114 is not allowed to be taken at present in step 408. In step 409, the controller 150 extracts and generates a warning voice, i.e. Imposer medication voice, from the voice medication database (not shown), and then proceeds to step 410.

Afterwards, in step 410, the controller 150 designates a color of the LED 115 of the corresponding container 114. In step 411, the controller 150 transmits information on the medication to the server 10 so as to automatically record the information. Here, the color of the LED 115 can be designated as, for instance, a red color.

Next, the process of recognizing the notification situation to generate service corresponding to the notification situation will be described in detail with reference to the attached drawings.

Figure 8:
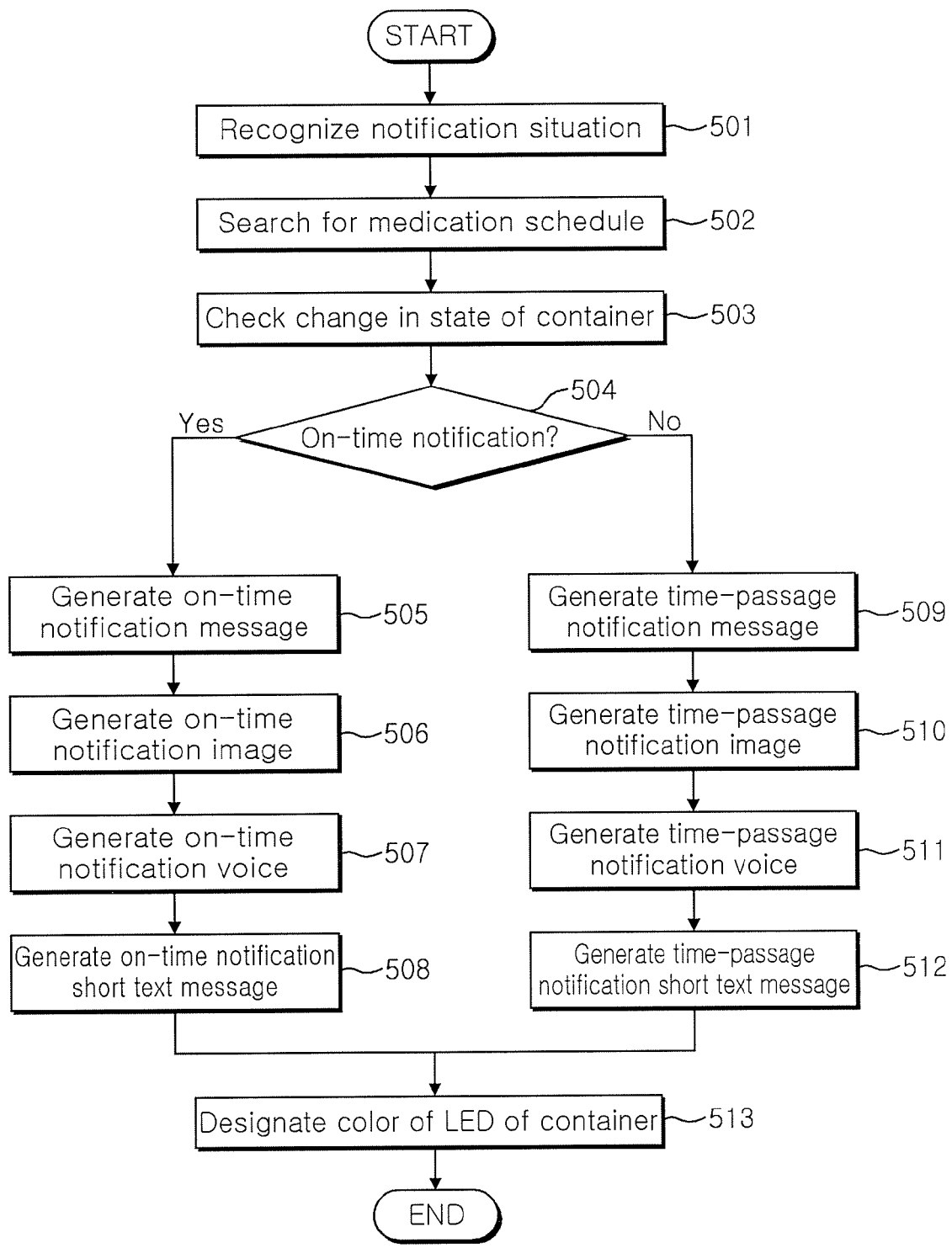
FIG. 8 is a flow chart illustrating a process of generating a service based on a notification situation in accordance with an exemplary embodiment of the present invention.

FIG. 8 is a flow chart illustrating a process of generating a service based on a notification situation in accordance with an exemplary embodiment of the present invention.

Referring to FIG. 8, in step 501, the controller 150 of the apparatus for assisting medication 100 recognizes a present situation as a notification situation using state data including the user ID, distance and medication box ID recognized in step 301 of FIG. 6, the medication schedule of the medication box, and the state of the container.

Then, in step 502, the controller 150 searches for a medication schedule corresponding to a current time. In step 503, the controller 150 checks a present state of the container 114 corresponding to the searched medication schedule.

Afterwards, in step 504, the controller 150 checks the type of service, and determines whether or not the notification is an on-time notification. As a result of the determination, when the on-time notification is determined, the controller 150 recognizes that the current time is set for the medication schedule and that the medication is contained in the container 114 corresponding to the medication schedule, and thus generates an on-time notification message on the basis of such recognition in step 505. Then, the controller 150 generates an on-time notification image in step 506, and on-time notification voice in step 507. Subsequently, in step 508, the controller 150 generates an on-time notification short text message for a short message service (SMS) which is to be transmitted to the mobile phone of a medication user, his or her family or a caregiver thereof, and then proceeds to step 513.

In contrast, as a result of the determination of step 504, when an on-time notification is not determined, the controller 150 recognizes that there is no medication schedule and that the medication is still contained in the corresponding container 114, and thus generates a time-passage notification message (to notify the lapse of medication time) on the basis of such recognition in step 509. Then, the controller 150 generates a time-passage notification image in step 510, and time-passage notification voice in step 511. Subsequently, in step 512, the controller 150 generates a time-passage notification short text message which is to be transmitted to the mobile phone of the user, his/her family or a caregiver thereof, and then proceeds to step 513.

In step 513, the controller 150 designates a color of the LED 115 of the container 114 when the time to take the medication in the container 114 has lapsed. Here, the color of the LED 115 can be designated as, for instance, a blue color.

Next, the process of providing information about the medication schedule of a day when no specific situation takes place will be described in detail with reference to the attached drawings. Here, whether or not a specific situation takes place is determined by checking whether any situation takes place by periods or at a specific time. A case in which the specific situation does not take place can include a case in which the specific situation such as the aforementioned medication or notification situation does not take place, or a case in which a change in database such as update of the medication schedule is intended to be transmitted to the user.

Figure 9:
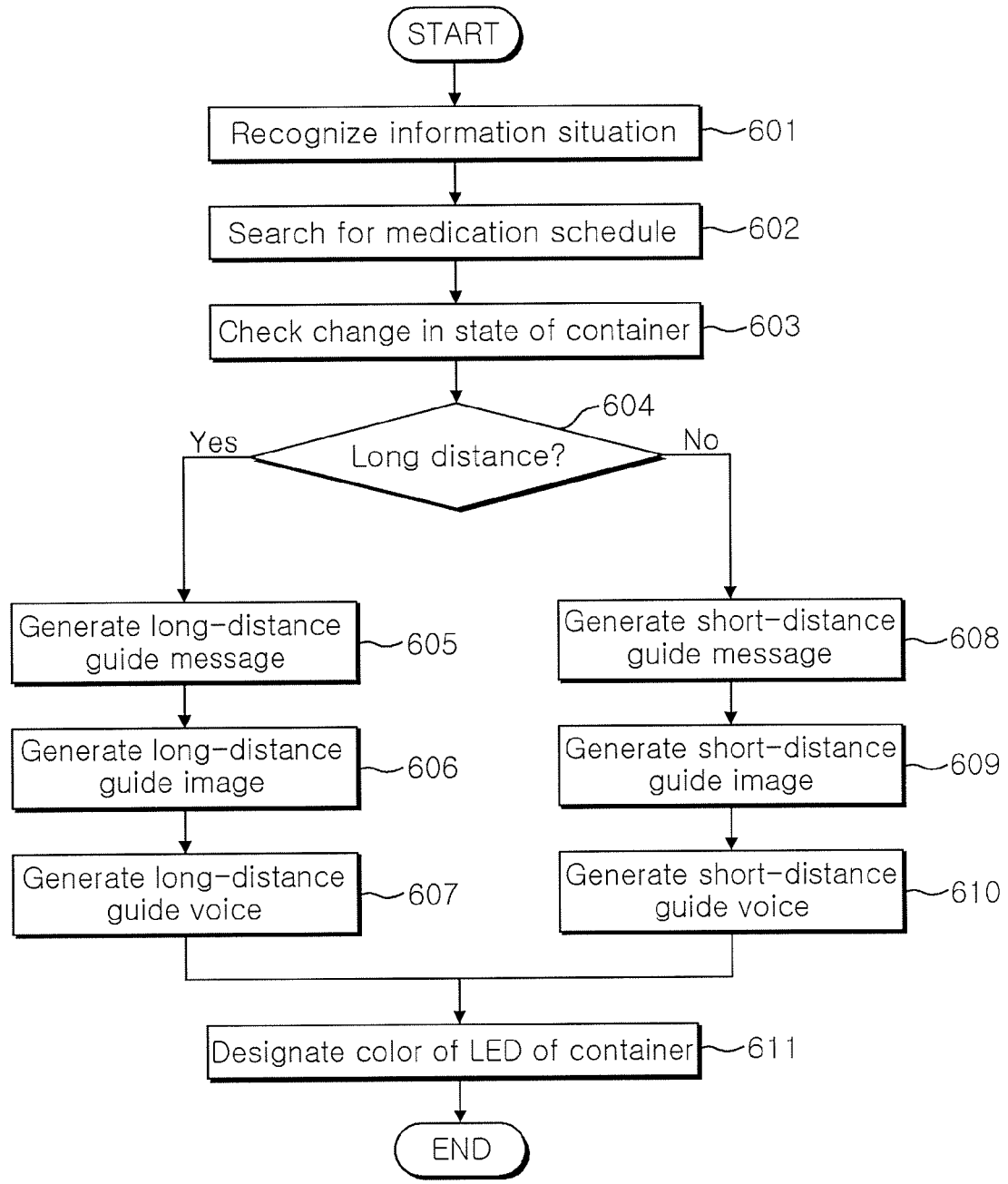
FIG. 9 is a flow chart illustrating a process of providing information about a medication schedule of that day in accordance with an exemplary embodiment of the present invention.

FIG. 9 is a flow chart illustrating a process of providing information about a medication schedule of that day in accordance with an exemplary embodiment of the present invention.

Referring to FIG. 9, in step 601, the controller 150 of the apparatus for assisting medication 100 recognizes a present situation as an information situation using state data including the user ID, distance and medication box ID recognized in step 301 of FIG. 6, the medication schedule of the medication box, and the state of the container.

Then, in step 602, the controller 150 searches for a medication schedule corresponding to that day. In step 603, the controller 150 checks the present state of the container 114 corresponding to the searched medication schedule.

Afterwards, in step 604, the controller 150 checks whether a user is located a long distance or a short distance away from the medication box at present. As a result of determination, when the user is located a long distance, the controller 150 generates service that provides information about present medication situation to the long-distance user. In detail, the controller 150 generates a long-distance guide message in step 605, and a long-distance guide image in step 606. In step 607, the controller 150 reads out medication voice information from a voice medication database to generate long-distance guide voice, and then proceeds to step 611.

In contrast, as a result of the determination of step 604, when the medication user is located a short distance at present, the controller 150 generates the service that provides the information about the present medication situation to the short-distance user. In detail, the controller 150 generates a short-distance guide message in step 608, and a short-distance guide image in step 609. In step 610, the controller 150 reads out the medication voice information from the voice medication database to generate short-distance guide voice, and then proceeds to step 611.

In step 611, the controller 150 designates a color of the LED 115 of the corresponding container 114. Here, the color of the LED 115 can be designated as, for instance, a blue color.

As described above, the services created on the basis of the respective situations can be transmitted to and realized through the corresponding apparatus. For example, when the created service is the message or image, the message or image is displayed on the display unit 140. When the created service is the voice, the voice is output through the loudspeaker (not shown). When the created service is a color of the LED, the color is displayed through the LED 115 of the medication box. When the created service is an SMS text message, the SMS text message is transmitted to the mobile phone of the user, his/her family or the caregiver thereof.

Meanwhile, according to an exemplary embodiment of the present invention, the medication schedule can be automatically generated with respect to a single prescription. This process will be described in detail with reference to FIG. 10.

Figure 10:
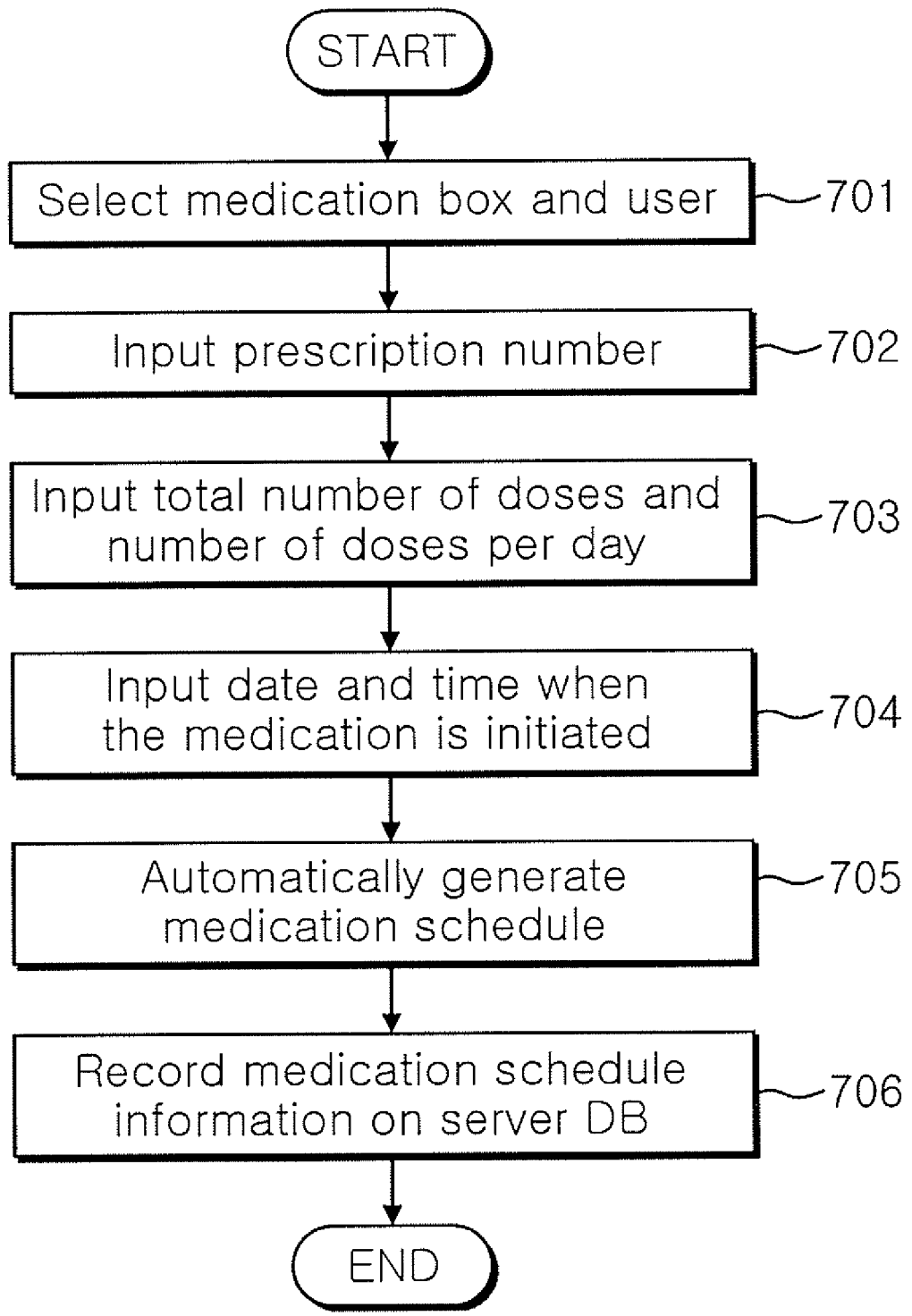
FIG. 10 is a flow chart illustrating a process of automatically generating a medication schedule with respect to a single prescription.

Referring to FIG. 10, a pharmacist or a manager selects a user who is intended to take medication and a medication box to be used in step 701, and then inputs information as prescribed (a prescription number, the total number of doses, the number of doses per day, date and time when the medication is initiated) in steps 702 through 704. Then, the controller 150 automatically generates all the medication schedules of the prescription using the input information in step 705. Further, the controller 150 transmits information about the generated medication schedules to the server 10, and records the information on a corresponding database (not shown) installed in the server 10 in step 706. Here, the medication schedules are described to be automatically generated by the controller 150, but they may be automatically generated by the server 10.

Thus, the present invention checks the spatial-temporal situation of the user to provide service corresponding to the checked situation, so that it can assist the user so as to be able to take an accurate dose of medication on time, and thus enhance the user's adaptability to medication.

Further, the present invention can notify the time to take the medication in different fashions according to a distance between the medication box and the user, and guide the medication to be taken at present such that the user can take an accurate dose of medication on time.

Furthermore, the present invention can accurately display the medication to be taken at a preset time according to the mediation schedule, and determine whether or not the medication to be taken exists to thereby detect and notify the medication of the user with accuracy.

Although a few exemplary embodiments of the present invention have been shown and described, it will be appreciated by those skilled in the art that modifications and variations can be made in these exemplary embodiments without departing from the principles and spirit of the invention, the scope of which is defined in the appended claims and their equivalents.

What is claimed is:

1. An apparatus for assisting medication comprising:
   a medication box storing a dose of medication to be taken at one time according to a medication schedule;
   a radio frequency receiver receiving a radio frequency signal from a radio frequency transmitter carried on a user, and extracting radio frequency signal information including information for recognizing the user from the received radio frequency signal;
   a controller receiving the radio frequency signal information extracted by the radio frequency receiver, creating and providing medication services based on a spatial-temporal situation of the user which are checked using the received radio frequency signal information, and detecting discharge of the medication from the medication box to check whether or not the user takes the medication; and a display unit displaying a result of checking whether or not the user takes the medication and information about the medication services.

2. The apparatus of claim 1, wherein the medication box includes:

a plurality of medication storage containers, each of which stores a dose of medication to be taken at one time according to the medication schedule and detects whether or not the stored medication exists using infrared radiation;

at least one light emitting diode allocated to each medication storage container, and showing a medication situation related to the medication stored in each medication storage container; and a liquid crystal display notifying the medication of the medication stored in each medication storage container according to the medication schedule.

3. The apparatus of claim 1, wherein the controller searches for identifications of the user and medication box mapped to an identification of the radio frequency transmitter which is included in the radio frequency signal information through a preset user mapping table to thereby recognize the user and medication box, and searches for a distance mapped to strength of the radio frequency signal included in the radio frequency signal information through a preset radio frequency signal mapping table to thereby recognize the distance.

4. The apparatus of claim 3, wherein the controller checks the situation of the user using the identifications of the recognized user and medication box, the distance, the medication schedule of the recognized user, a current time, and a present state of each medication storage container allocated to the recognized user.

5. The apparatus of claim 4, wherein the checked situation is divided into a medication situation indicating details associated with the medication, a notification situation indicating notification of the medication, and an information situation providing information about the corresponding medication schedule and a state of the medication to the recognized user under an environment where the other situations do not take place.

6. The apparatus of claim 1, wherein the controller automatically creates and stores all the medication schedules with respect to a single prescription when information about the user intended to take medication, the medication box and the prescription is input.

7. A method for assisting medication using an apparatus for assisting medication having a medication box, the method comprising:

extracting radio frequency signal information including information for recognizing a user from a radio frequency signal received from the user;

recognizing the user using the extracted radio frequency signal information, and checking a spatial-temporal situation of the recognized user;

examining a present state of each medication storage container of the medication box in which the medications to be taken by the recognized user are stored;

creating medication services based on the recognized situation; and providing the created medication services.

8. The method of claim 7, wherein the extracting of the radio frequency signal information includes:

recognizing the user mapped to an identification of a radio frequency transmitter which is included in the radio frequency signal information on a preset user mapping table;

checking an identification of the medication box of the recognized user on the preset user mapping table;

checking a distance, which is spaced apart from the user and is mapped to strength of the radio frequency signal included in the radio frequency signal information on a preset radio frequency signal mapping table; and checking a current time and a medication schedule of the recognized user.

9. The method of claim 7, wherein the examining of the present state of each medication storage container includes:

measuring an output voltage of each medication storage container which is a result of detecting whether or not the stored medication exists using infrared radiation transmitted at each medication storage container;

determining that the medication is not stored in each medication storage container when a level of the measured output voltage is higher than a critical level;

determining that the medication is stored in each medication storage container when the level of the measured output voltage is lower than the critical level; and displaying the situation corresponding to a result of determining whether or not the medication is stored in each medication storage container.

10. The method of claim 7, wherein the creating of the medication services includes: when the spatial-temporal situation of the recognized user is recognized as a medication situation, checking a change in state of each medication storage container that stores a dose of medication to be taken at one time according to a medication schedule;

determining a type of the medication service with respect to each medication storage container, the state of which is changed, using a preset user mapping table;

creating the medication service corresponding to the determined medication service type; and displaying the state of each medication storage container, the state of which is changed.

11. The method of claim 10, wherein the creating of the medication service corresponding to the determined medication service type includes:

when the determined medication service type belongs to proper medication, generating a medication assisting message, a medication assisting image, and medication assisting voice based on corresponding voice read out from a preset medication voice database; and when the determined medication service type belongs to improper medication, generating an improper medication message, an improper medication image, and improper medication voice based on corresponding voice read out from the preset medication voice database.

12. The method of claim 7, wherein the creating of the medication services includes: when the spatial-temporal situation of the recognized user is recognized as a notification situation, searching for a medication schedule corresponding to a current time using state data associated with the recognized notification situation;

checking a state of the corresponding medication storage container that stores the medication to be taken corresponding to the searched medication schedule;

determining a type of the medication service on a basis of whether or not the medication to be taken is stored in the corresponding medication storage container;

creating the medication service corresponding to the determined medication service type; and displaying the state of the corresponding medication storage container.

13. The method of claim 12, wherein the creating of the medication service corresponding to the determined medication service type includes:

when the current time is set for the medication schedule and when the medication is stored in the corresponding medication storage container, generates an on-time notification message, an on-time notification image, on-time notification voice based on corresponding voice read out from a preset medication voice database, and an on-time notification short text message; and when the current time is not set for the medication schedule and when the medication is stored in the corresponding medication storage container, generates a time-passage notification message, a time-passage notification image, time-passage notification voice based on corresponding voice read out from the preset medication voice database, and a time-passage notification short text message.

14. The method of claim 7, wherein the creating of the medication services includes: when the spatial-temporal situation of the recognized user is recognized as an information situation, searching for a medication schedule corresponding to a day using state data associated with the recognized information situation;

checking a state of the corresponding medication storage container that stores the medication to be taken corresponding to the searched medication schedule;

checking a distance spaced apart from the recognized user;

creating the medication service providing information about a present medication situation to the user on a basis of the checked distance; and displaying the state of the corresponding medication storage container.

15. The method of claim 14, wherein the creating of the medication service providing information about the present medication situation to the user includes:

when the user is located a long distance, generating a long-distance guide message, a long-distance guide image, and long-distance guide voice based on corresponding voice read out from a preset medication voice database; and when the user is located a short distance, generating a short-distance guide message, a short-distance guide image, and short-distance guide voice based on corresponding voice read out from the preset medication voice database.

* * * * *